United States Patent [19]
Albone et al.

[11] Patent Number: 6,090,579
[45] Date of Patent: Jul. 18, 2000

[54] HUMAN SDR2 CDNA CLONE

[75] Inventors: Earl Francis Albone, Conshohocken; Kristine Kay Kikly, Linfield, both of Pa.

[73] Assignee: SmithKline Beecham Corporation, Philadelphia, Pa.

[21] Appl. No.: 08/991,813

[22] Filed: Dec. 16, 1997

Related U.S. Application Data

[60] Provisional application No. 60/055,375, Aug. 12, 1997.
[51] Int. Cl.[7] .................................................. C12N 15/00
[52] U.S. Cl. .................... 435/69.1; 435/69.6; 435/252.3; 435/455; 536/23.5
[58] Field of Search ................................ 435/320.1, 325, 435/69.1, 172.3, 252.3–252.35; 536/23.1, 23.5

[56] References Cited

PUBLICATIONS

Genbank Accession #N39774.
Genbank Accession #Z96934.
HGS Est #1688378.
George et al, in Macromolecular Sequencing and Synthesis Selected Methods and Applications, Schlesinger (ed.), Alan R. Liss, Inc., New York, NY, pp. 127–149., (1988).
Shirozu et al, Genomics 37: 273 (1996).

*Primary Examiner*—James Martinell
*Attorney, Agent, or Firm*—William T. Han; Ratner & Prestia; William T. King

[57] ABSTRACT

SDR2 polypeptides and polynucleotides and methods for producing such polypeptides by recombinant techniques are disclosed. Also disclosed are methods for utilizing SDR2 polypeptides and polynucleotides in the design of protocols for the treatment of cancer, inflammation, autoimmunity, allergy, asthma, rheumatoid arthritis, CNS inflamation, cerebellar degeneration, Alzheimer's disease, Parkinsons disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections, among others, and diagnostic assays for such conditions.

11 Claims, No Drawings

HUMAN SDR2 CDNA CLONE

This application claims the benefit of U.S. Provisional Application No. 60/055,375, filed Aug. 12, 1997.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to 6-TM family, hereinafter referred to as SDR2 (stromal-cell derived receptor). The invention also relates to inhibiting or activating the action of such polynucleotides and polypeptides.

BACKGROUND OF THE INVENTION

Murine SDR2 was cloned from a bone marrow stromal cell line using a signal sequence trap method (Shirozu, M., et al., Genomics 37:273–280, 1996). Murine SDR2 contains a signal sequence and has six putative transmembrane spanning domains. Other six transmembrane spanning proteins function as ion transporters (Becker, D., et al., PNAS 93:8123–8128, 1996), water channel proteins (Misaka, T., et al., FEBS Lett. 381:208–212, 199; Jung, J. S., et al., PNAS 91:13052–13056, 1994), iron transporters (Dix, D. R., et al., JBC 269:26092–26099, 1994) or have been linked to cellular activation and division (Gaugitsch, H. W., et al., JBC 267:11267–11273, 1992). This indicates that the 6-TM family has an established, proven history as therapeutic targets. Clearly there is a need for identification and characterization of further members of 6-TM family which can play a role in preventing, ameliorating or correcting dysfunctions or diseases, including, but not limited to, cancer, inflammation, autoimmunity, allergy, asthma, rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections.

SUMMARY OF THE INVENTION

In one aspect, the invention relates to SDR2 polypeptides and recombinant materials and methods for their production. Another aspect of the invention relates to methods for using such SDR2 polypeptides and polynucleotides. Such uses include the treatment of cancer, inflammation, autoimmunity, allergy, asthma, rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections, among others. In still another aspect, the invention relates to methods to identify agonists and antagonists using the materials provided by the invention, and treating conditions associated with SDR2 imbalance with the identified compounds. Yet another aspect of the invention relates to diagnostic assays for detecting diseases associated with inappropriate SDR2 activity or levels.

DESCRIPTION OF THE INVENTION

Definitions

The following definitions are provided to facilitate understanding of certain terms used frequently herein.

"SDR2" refers, among others, generally to a polypeptide having the amino acid sequence set forth in SEQ ID NO:2 or an allelic variant thereof.

"SDR2 activity or SDR2 polypeptide activity" or "biological activity of the SDR2 or SDR2 polypeptide" refers to the metabolic or physiologic function of said SDR2 including similar activities or improved activities or these activities with decreased undesirable side-effects. Also included are antigenic and immunogenic activities of said SDR2.

"SDR2 gene" refers to a polynucleotide having the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-inking, cyclization, disulfide bond formation, demethylation, formation of covalent crosslinks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A.M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988)48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO:1 is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to SDR2 polypeptides (or SDR2 proteins). The SDR2 polypeptides include the polypeptide of SEQ ID NOS:2 and 4; as well as polypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO: 2. Furthermore, those with at least 97–99% are highly preferred. Also included within SDR2 polypeptides are polypeptides having the amino acid sequence which have at least 80% identity to the polypeptide having the amino acid sequence of SEQ ID NO:2 over its entire length, and still more preferably at least 90% identity, and still more preferably at least 95% identity to SEQ ID NO:2. Furthermore, those with at least 97–99% are highly preferred. Preferably SDR2 polypeptide exhibit at least one biological activity of SDR2.

The SDR2 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the SDR2 polypeptides are also included in the invention. A fragment is a polypeptide having an amino acid sequence that entirely is the same as part, but not all, of the amino acid sequence of the aforementioned SDR2 polypeptides. As with SDR2 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of SDR2 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of SDR2 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate SDR2 activity, including those with a similar activity or an improved activity, or with a decreased undesirable activity. Also included are those that are antigenic or immunogenic in an animal, especially in a human.

Preferably, all of these polypeptide fragments retain the biological activity of the SDR2, including antigenic activity. Among the most preferred fragment is that having the amino acid sequence of SEQ ID NO:4. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr, among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The SDR2 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to SDR2 polynucleotides. SDR2 polynucleotides include isolated polynucleotides which encode the SDR2 polypeptides and fragments, and polynucleotides closely related thereto. More specifically, SDR2 polynucleotide of the invention include a polynucleotide comprising the nucleotide sequence contained in SEQ ID NO:1 encoding a SDR2 polypeptide of SEQ ID NO:2, and polynucleotides having the particular sequences of SEQ ID NOS:1 and 3. SDR2 polynucleotides further include a polynucleotide comprising a nucleotide sequence that has at least 80% identity over its entire length to a nucleotide sequence encoding the SDR2 polypeptide of SEQ ID NO:2, and a polynucleotide comprising a nucleotide sequence that is at least 80% identical to that of SEQ ID NO:1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under SDR2 polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such SDR2 polynucleotides.

SDR2 of the invention is structurally related to other proteins of the 6-TM family, as shown by the results of sequencing the cDNA encoding human SDR2. The cDNA sequence of SEQ ID NO:1 contains an open reading frame (nucleotide number 10 to 1785) encoding a polypeptide of 592 amino acids of SEQ ID NO:2. The amino acid sequence of Table 1 (SEQ ID NO:2) has about 78% identity (using BESTFIT) in 592 amino acid residues with murine SDR2 (Shirozu, M. et al. Genomics 37:273–280, 1996). The nucleotide sequence of Table 1 (SEQ ID NO:1) has about 78% identity (using BESTFIT) in 1803 nucleotide residues with murine SDR2 (Shirozu, M. et al. Genomics 37:273–280, 1996). Thus, SDR2 polypeptides and polynucleotides of the present invention are expected to have, inter alia, similar biological functions/properties to their homologous polypeptides and polynucleotides, and their utility is obvious to anyone skilled in the art.

TABLE 1[a]

```
   1 TTTTATCAGA TGGCAGTTTC TGGATTTACT CTTGGTACCT GCATACTTCT
  51 GTTGCACATT AGTTATGTGG CTAATTATCC CAATGGAAAA GTAACACAGT
 101 CATGCCATGG AATGATTCCT GAACATGGTC ATAGTCCACA GTCTGTTCCT
 151 GTTCATGACA TTTACGTGAG TCAGATGACA TTCAGGCCAG GAGATCAGAT
 201 TGAAGTTACT TTGTCAGGGC ATCCATTTAA AGGCTTTCTC CTAGAAGCGC
 251 GTAATGCTGA GGATCTGAAT GGCCCTCCTA TTGGCTCCTT CACATTGATT
 301 GACAGTGAAG TGTCACAACT TTTGACCTGT GAAGATATAC AGGGATCAGC
 351 AGTGAGTCAC AGGAGTGCAT CTAAAAAAAC AGAAATTAAA GTCTACTGGA
 401 ATGCTCCAAG CAGTGCTCCA AATCACACAC AGTTTCTAGT CACAGTTGTT
 451 GAGAAGTATA AAATCTACTG GGTGAAGATT CCTGGTCCTA TAATTTCACA
 501 ACCAAATGCA TTTCCTTTTA CAACACCTAA AGCTACAGTA GTACCTTTGC
 551 CAACGTTACC TCCCGTTTCC CACTTAACCA AACCATTCAG TGCCTCAGAT
 601 TGTGGGAACA AGAAGTTCTG TATTAGGAGT CCTTTGAACT GTGACCCAGA
 651 GAAGGAGGCT TCCTGTGTCT TCTTGTCCTT CACAAGAGAT GACCAATCGG
 701 TGATGGTTGA AATGAGCGGC CCCAGTAAAG GCTATTTATC CTTTGCATTG
 751 TCTCATGATC AGTGGATGGG TGATGATGAT GCTTATCTGT GTATTCATGA
 801 AGATCAGACT GTGTACATCC AGCCTTCCCA TTTAACGGGG CGAAGTCACC
 851 CTGTAATGGA CTCCAGGGAT ACCCTTGAGG ATATGGCTTG GAGGTTGGCG
 901 GACGGTGTTA TGCAGTGTTC TTTCAGAAGA AACATTACCC TTCCTGGAGT
 951 TAAGAATAGA TTTGATCTAA ACACAAGCTA TTACATATTT CTAGCAGATG
1001 GTGCAGCTAA TGATGGTCGA ATTTACAAGC ACTCTCAGCA ACCTTTGATT
1051 ACCTATGAAA AATATGATGT GACAGACTCT CCAAAGAACA TAGGAGGATC
1101 CCATTCTGTA CTCCTTCTGA AGGTTCATGG TGCCTTAATG TTTGTGGCAT
1151 GGATGACTAC TGTTAGCATA GGTGTACTGG TTGCCCGGTT CTTCAAGCCA
1201 GTTTGGTCAA AAGCTTTCTT GCTTGGTGAA GCAGCTTGGT TTCAGGTGCA
1251 TCGGATGCTC ATGTTCACCA CAACTGTCCT CACCTGCATT GCTTTTGTTA
1301 TGCCGTTTAT ATACAGGGGA GGCTGGAGTA GGCATGCAGG TTACCACCCA
1351 TACCTCGGCT GTATAGTGAT GACTTTGGCA GTTCTTCAGC TCTTCTGGC
1401 AGTCTTCAGG CCACCTTTAC ATGACCCAAG AAGGCAAATG TTTAACTGGA
1451 CTCATTGGAG TATGGGAACA GCTGCTAGAA TAATAGCAGT GGCAGCGATG
1501 TTCCTGGGAA TGGATTTACC AGGACTGAAT CTTCCTGATT CATGGAAAAC
1551 CTATGCAATG ACCGGATTCG TAGCCTGGCA TGTTGGGACT GAGGTTGTTC
1601 TGGAGGTACA TGCTTATCGG CTCTCTCGCA AAGTTGAAAT ATTGGATGAT
1651 GACAGAATTC AGATCCTTCA GTCATTTACT GCAGTGGAAA CAGAGGGTCA
1701 TGCTTTTAAA AAGGCAGTGT TGGCAATTTA TGTCTGTGGG AATGTTACTT
1751 TTCTCATCAT ATTTTTATCT GCAATCAACC ATCTATGAGC AAGACTCTGT
1801 CTC
```

[a]A nucleotide sequence of a human SDR2 (SEQ ID NO: 1).

TABLE 2[b]

```
  1 MAVSGFTLGT CILLLHISYV ANYPNGKVTQ SCHGMIPEHG HSPQSVPVHD

51 IYVSQMTFRP GDQIEVTLSG HPFKGFLLEA RNAEDLNGPP IGSFTLIDSE

101 VSQLLTCEDI QGSAVSHRSA SKKTEIKVYW NAPSSAPNHT QFLVTVVEKY

151 KIYWVKIPGP IISQPNAFPF TTPKATVVPL PTLPPVSHLT KPFSASDCGN

201 KKFCIRSPLN CDPEKEASCV FLSFTRDDQS VMVEMSGPSK GYLSFALSHD

251 QWMGDDDAYL CIHEDQTVYI QPSHLTGRSH PVMDSRDTLE DMAWRLADGV

301 MQCSFRRNIT LPGVKNRFDL NTSYYIFLAD GAANDGRIYK HSQQPLITYE

351 KYDVTDSPKN IGGSHSVLLL KVHGALMFVA WMTTVSIGVL VARFFKPVWS

401 KAFLLGEAAW FQVHRMLMFT TTVLTCIAFV MPFIYRGGWS RHAGYHPYLG

451 CIVMTLAVLQ PLLAVFRPPL HDPRRQMFNW THWSMGTAAR IIAVAAMFLG

501 MDLPGLNLPD SWKTYAMTGF VAWHVGTEVV LEVHAYRLSR KVEILDDDRI

551 QILQSFTAVE TEGHAFKKAV LAIYVCGNVT FLIIFLSAIN HL
```

[b]An amino acid sequence of a human SDR2 (SEQ ID NO: 2).

One polynucleotide of the present invention encoding SDR2 may be obtained using standard cloning and screening, from a cDNA library derived from mRNA in cells of human primary dendritic cells, liver, and fetal liver using the expressed sequence tag (EST) analysis (Adams, M.D., et al. *Science* (1991) 252:1651–1656; Adams, M. D. et al., *Nature,* (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding SDR2 polypeptide of SEQ ID NO:2 may be identical to the polypeptide encoding sequence contained in Table 1 (nucleotide number 10 to 1785 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of SDR2 polypeptide, the polynucleotide may include the coding sequence for the mature polypeptide or a fragment thereof by itself; the coding sequence for the mature polypeptide or fragment in reading frame with other coding sequences, such as those encoding a leader or secretory sequence, a pre-, or pro- or preproprotein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci U.S.A.* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding SDR2 variants comprising the amino acid sequence of SDR2 polypeptide of Table 2 (SEQ ID NO:2) in which several, 5–10, 1–5, 1–3, 1–2 or 1 amino acid residues are substituted, deleted or added, in any combination. Among the preferred polynucleotides of the present invention is contained in Table 3 (SEQ ID NO:3) encoding the amino acid sequence of Table 4 (SEQ ID NO:4).

TABLE 3[c]

```
  1 GGTTCATGAC ATTTACGTGA GTCAGATGAC ATTCAGGCCA GGAGATCAGA

51 TTGAAGTTAC TTTGTCAGGG CATCCATTTA AAGGCTTTCT CCTAGAAGCG

101 CGTAATGCTG AGGATCTGAA TGGCCCTCCT ATTGGCTCCT TCACATTGAT

151 TGACAGTGAA GTGTCACAAC TTTTGACCTG TGAAGATATA CAGGGGATCA

201 GCAGTGAGTC ACAGAAGTGG CATCTGAAAA AAACAGAAAT TAAAGTCTAC

251 TGGGAAGCTC CAAGCAGTGG CTCCCAAATG CACACACAGT TTCTAGTGAC

301 AGTTGTTGAG AAGATGAAAA TCTACTGGGT GAAGATTNCC TGGTGCCCAT

351 GATTTTGCAC AACCAAANGG CATTTGCCTT TTTTACNAAC A
```

[c]A partial nucleotide sequence of a human SDR2 (SEQ ID NO: 3).

TABLE 4[d]

```
  1 VHDIYVSQMT FRPGDQIEVT LSGHPFKGFL LEARNAEDLN GPPIGSFTLI

51 DSEVSQLLTC EDIQGISSES QKWHLKKTEI KVYWEAPSSG SQMHTQFLVT

101 VVEKMKIYWV KI
```

[d]A partial amino acid sequence of a human SDR2 (SEQ ID NO: 4).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1 or a fragment thereof (including that of SEQ ID NO:3), may be used as hybridization probes for cDNA and genomic DNA, to isolate full-length cDNAs and genomic clones encoding SDR2 polypeptide and to isolate cDNA and genomic clones of other genes (including genes encoding homologs and orthologs from species other than human) that have a high sequence similarity to the SDR2 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding SDR2 polypeptide, including homologs and orthologs from species other than human, comprises the steps of screening an appropriate library under stingent hybridization conditions with a labeled probe having the SEQ ID NO:1 or a fragment thereof (including that of SEQ ID NO:3), and isolating full-length cDNA and genomic clones containing said polynucleotide sequence. Such hybridization techniques are well known to those of skill in the art. Thus in another aspect, SDR2 polynucleotides of the present invention further include a nucleotide sequence comprising a nucleotide sequence that hybridize under stringent condition to a nucleotide sequence having SEQ ID NO:1 or a fragment thereof (including that of SEQ ID NO:3). Also included with SDR2 polypeptides are polypeptide comprising amino acid sequence encoded by nucleotide sequence obtained by the above hybridization condition. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA, followed by washing the filters in 0.1× SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., *BASIC METHODS IN MOLECULAR BIOLOGY* (1986) and Sambrook et al., *MOLECULAR CLONING: A LABORATORY MANUAL,* 2nd Ed., Cold Spring Harbor Laboratory Press, Cold Spring Harbor, N.Y. (1989) such as calcium phosphate transfection, DEAE-dextran mediated transaction, transvection, microinjection, cationic lipid-mediated transfection, electroporation, transduction, scrape loading, ballistic introduction or infection.

Representative examples of appropriate hosts include bacterial cells, such as streptococci staphylococci, *E. coli, Streptomyces* and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the SDR2 polypeptide is to be expressed for use in screening assays, generally, it is preferred that the polypeptide be produced at the surface of the cell. In this event, the cells may be harvested prior to use in the screening assay. If SDR2 polypeptide is secreted into the medium, the medium can be recovered in order to recover and purify the polypeptide; if produced intracellularly, the cells must first be lysed before the polypeptide is recovered. SDR2 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of SDR2 polynucleotides for use as diagnostic reagents. Detection of a mutated form of SDR2 gene associated with a dysfunction will provide a diagnostic tool that can add to or define a diagnosis of a disease or susceptibility to a disease which results from under-expression, over-expression or altered expression of SDR2. Individuals carrying mutations in the SDR2 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled SDR2 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et al, *Proc Natl Acad Sci U.S.A.* (1985) 85: 4397–4401. In another embodiment, an array of oligonucleotides probes comprising SDR2 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., *Science,* Vol 274, pp 610–613 (1996)).

The diagnostic assays offer a process for diagnosing or determining a susceptibility to cancer, inflammation, autoimmunity, allergy, asthma, rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections through detection of mutation in the SDR2 gene by the methods described.

In addition, cancer, inflammation, autoimmunity, allergy, asthma, rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections, can be diagnosed by methods comprising determining from a sample derived from a subject an abnormally decreased or increased level of SDR2 polypeptide or SDR2 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an SDR2 polypeptide, in a sample derived from a host are well-known to those of skill in the art. Such assay methods include radioimmunoassays, competitive-binding assays, Western Blot analysis and ELISA assays.

Thus in another aspect, the present invention relates to a diagonostic kit for a disease or suspectability to a disease, particularly cancer, inflammation, autoimmunity, allergy, asthma, rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections, which comprises:

(a) a SDR2 polynucleotide, preferably the nucleotide sequence of SEQ ID NO:1, or a fragment thereof;

(b) a nucleotide sequence complementary to that of (a);

(c) a SDR2 polypeptide, preferably the polypeptide of SEQ ID NO:2, or a fragment thereof; or (d) an antibody to a SDR2 polypeptide, preferably to the polypeptide of SEQ ID NO:2.

It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof or cells expressing them can also be used as immunogens to produce antibodies immunospecific for the SDR2 polypeptides. The term "immunospecific" means that the antibodies have substantial greater affinity for the polypeptides of the invention than their affinity for other related polypeptides in the prior art.

Antibodies generated against the SDR2 polypeptides can be obtained by administering the polypeptides or epitope-bearing fragments, analogs or cells to an animal preferably a nonhuman, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against SDR2 polypeptides may also be employed to treat cancer, inflammation, autoimmunity, allergy, asthma, rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections, among others.

Vaccines

Another aspect of the invention relates to a method for inducing an immunological response in a mammal which comprises inoculating the mammal with SDR2 polypeptide, or a fragment thereof, adequate to produce antibody and/or T cell immune response to protect said animal from cancer, inflammation, autoimmunity, allergy, asthma, rheumatoid arthritis, CNS inflammation, cerebellar degeneration, Alzheimer's disease, Parkinsons disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections, among others. Yet another aspect of the invention relates to a method of inducing immunological response in a mammal which comprises, delivering SDR2 polypeptide via a vector directing expression of SDR2 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a SDR2 polypeptide wherein the composition comprises a SDR2 polypeptide or SDR2 gene. The vaccine formulation may further comprise a suitable carrier. Since SDR2 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The SDR2 polypeptide of the present invention may be employed in a screening process for compounds which activate (agonists) or inhibit activation of (antagonists, or otherwise called inhibitors) the SDR2 polypeptide of the present invention. Thus, polypeptides of the invention may also be used to assess identify agonist or antagonists from, for example, cells, cell-free preparations, chemical libraries, and natural product mixtures. These agonists or antagonists may be natural or modified substrates, ligands, enzymes, receptors, etc., as the case may be, of the polypeptide of the present invention; or may be structural or functional mimetics of the polypeptide of the present invention. See Coligan et al, Current Protocols in Immunology 1(2):Chapter 5 (1991).

SDR2 polypeptides are responsible for many biological functions, including many pathologies. Accordingly, it is desirous to find compounds and drugs which stimulate SDR2 polypeptide on the one hand and which can inhibit the function of SDR2 polypeptide on the other hand. In general, agonists are employed for therapeutic and prophylactic purposes for such conditions as cancer, inflammation, autoimmunity, allergy, asthma, rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections. Antagonists may be employed for a variety of therapeutic and prophylactic purposes for such conditions as cancer, inflamation, autoimmunity, allergy, asthma, rheumatoid arthritis, CNS inflammation, cerebellar degeneration, Alzheimer's disease, Parkinson's disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal, protozoan and viral infections.

In general, such screening procedures may involve using appropriate cells which express the SDR2 polypeptide or respond to SDR2 polypeptide of the present invention. Such cells include cells from mammals, yeast, Drosophila or *E. coli*. Cells which express the SDR2 polypeptide (or cell membrane containing the expressed polypeptide) or respond to SDR2 polypeptide are then contacted with a test compound to observe binding, or stimulation or inhibition of a functional response. The ability of the cells which were contacted with the candidate compounds is compared with the same cells which were not contacted for SDR2 activity.

The assays may simply test binding of a candidate compound wherein adherence to the cells bearing the SDR2 polypeptide is detected by means of a label directly or indirectly associated with the candidate compound or in an assay involving competition with a labeled competitor. Further, these assays may test whether the candidate compound results in a signal generated by activation of the SDR2 polypeptide, using detection systems appropriate to the cells bearing the SDR2 polypeptide. Inhibitors of activation are generally assayed in the presence of a known agonist and the effect on activation by the agonist by the presence of the candidate compound is observed.

Further, the assays may simply comprise the steps of mixing a candidate compound with a solution containing a SDR2 polypeptide to form a mixture, measuring SDR2 activity in the mixture, and comparing the SDR2 activity of the mixture to a standard.

The SDR2 cDNA, protein and antibodies to the protein may also be used to configure assays for detecting the effect of added compounds on the production of SDR2 mRNA and protein in cells. For example, an ELISA may be constructed for measuring secreted or cell associated levels of SDR2 protein using monoclonal and polyclonal antibodies by standard methods known in the art, and this can be used to discover agents which may inhibit or enhance the production of SDR2 (also called antagonist or agonist, respectively) from suitably manipulated cells or tissues.

The SDR2 protein may be used to identify membrane bound or soluble receptors, if any, through standard receptor binding techniques known in the art. These include, but are not limited to, ligand binding and crosslinking assays in which the SDR2 is labeled with a radioactive isotope (eg 125I), chemically modified (eg biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of SDR2 which compete with the binding of SDR2 to its receptors, if any. Standard methods for conducting screening assays are well understood in the art.

Examples of potential SDR2 polypeptide antagonists include antibodies or, in some cases, oligonucleotides or proteins which are closely related to the ligands, substrates, enzymes, receptors, etc., as the case may be, of the SDR2 polypeptide, e.g., a figment of the ligands, substrates, enzymes, receptors, etc.; or small molecules which bind to the polypeptide of the present invention but do not elicit a response, so that the activity of the polypeptide is prevented.

Thus in another aspect, the present invention relates to a screening kit for identifying agonists, antagonists, ligands, receptors, substrates, enzymes, etc. for SDR2 polypeptides; or compounds which decrease or enhance the production of SDR2 polypeptides, which comprises:

(a) a SDR2 polypeptide, preferably that of SEQ ID NO:2;

(b) a recombinant cell expressing a SDR2 polypeptide, preferably that of SEQ ID NO:2;

(c) a cell membrane expressing a SDR2 polypeptide; preferably that of SEQ ID NO:2; or (d) antibody to a SDR2 polypeptide, preferably that of SEQ ID NO:2.

It will be appreciated that in any such kit, (a), (b), (c) or (d) may comprise a substantial component.

Prophylactic and Therapeutic Methods

This invention provides methods of treating abnormal conditions such as, cancer, inflammation, autoimmunity, allergy, asthma, rheumatoid arthritis, CNS inflammation, cerebellar degeneration, Alzheimer's disease, Parkinsons disease, multiple sclerosis, amylotrophic lateral sclerosis, head injury damage, and other neurological abnormalities, septic shock, sepsis, stroke, osteoporosis, osteoarthritis, ischemia reperfusion injury, cardiovascular disease, kidney disease, liver disease, ischemic injury, myocardial infarction, hypotension, hypertension, AIDS, myelodysplastic syndromes and other hematologic abnormalities, aplastic anemia, male pattern baldness, and bacterial, fungal protozoan and viral infections, related to both an excess of and insufficient amounts of SDR2 polypeptide activity.

If the activity of SDR2 polypeptide is in excess, several approaches are available. One approach comprises administering to a subject an inhibitor compound (antagonist) as hereinabove described along with a pharmaceutically acceptable carrier in an amount effective to inhibit the function of the SDR2 polypeptide, such as, for example, by blocking the binding of ligands, substrates, enzymes, receptors, etc., or by inhibiting a second signal, and thereby alleviating the abnormal condition. In another approach, soluble forms of SDR2 polypeptides still capable of binding the ligand, substrate, enzymes, receptors, etc. in competition with endogenous SDR2 polypeptide may be administered. Typical embodiments of such competitors comprise fragments of the SDR2 polypeptide.

In another approach, soluble forms of SDR2 polypeptides still capable of binding the ligand in competition with endogenous SDR2 polypeptide may be administered. Typical embodiments of such competitors comprise fragments of the SDR2 polypeptide.

In still another approach, expression of the gene encoding endogenous SDR2 polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression,* CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an underexpression of SDR2 and its activity, several approaches are also available. One approach comprises administering to a subject a therapeutically effective amount of a compound which activates SDR2 polypeptide, i.e., an agonist as described above, in combination with a pharmaceutically acceptable carrier, to thereby alleviate the abnormal condition. Alternatively, gene therapy may be employed to effect the endogenous production of SDR2 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches,* (and references cited therein) in Human Molecular Genetics, T Strachan and A P Read, BIOS Scientific Publishers Ltd (1996). Another approach is to administer a therapeutic amount of SDR2 polypeptides in combination with a suitable pharmaceutical carrier.

Formulation and Administration

Peptides, such as the soluble form of SDR2 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are earned out using standard techniques, which are well known and routine to those of skill in the art, except where otherwise described in detail. The examples illustrate, but do not limit the invention.

Example 1

The gene expression profile of a variety of human tissues and cells, as determined by random sequencing of cDNA libraries, was searched for an expressed sequence tag (EST) with homology to known cDNA using the FASTA algorithm. This comparison yielded several gene "hits." Human SDR2 was first identified as an EST in a commercial database. Although there are several methods to obtain the full length cDNA two are outlined below.

1.) The method of Rapid Amplification of cDNA Ends (RACE) can be utilized to obtain the 5' end. See Frohman et al., Proc. Nat. Acad. Sci U.S.A. 85, 8998–9002. (1988). Briefly, specific oligonucleotides are annealed to mRNA and used to prime the synthesis of the cDNA strand. Following destruction of the mRNA with RNaseH, a poly-C anchor sequence is added to the 3' end of the cDNA and the resulting fragment is amplified using a 'nested' set of antisense primers and an anchor sequence primer. The amplified fragment is cloned into an appropriate vector and subjected to restriction and sequence analysis.

2.) The polymerase chain reaction can be used to amplify the 5' end of the cDNA from human cDNA libraries using sequential rounds of 'nested' PCR with two sets of primers. One set of antisense primers is specific to the 5' end of the partial cDNA and the other set of primers anneals to the vector specific sequence. The amplified products are cloned into an appropriate vector and subjected to restriction and sequence analysis.

All publications, including but not limited to patents and patent applications, cited in this specification are herein incorporated by reference as if each individual publication were specifically and individually indicated to be incorporated by reference herein as though fully set forth.

What is claimed is:

1. An isolated polynucleotide comprising a nucleotide sequence that encodes a polypeptide comprising the amino acid sequence set forth in SEQ ID NO:2.

2. The polynucleotide of claim 1 wherein said polynucleotide comprises the nucleotide sequence contained in SEQ ID NO:1 encoding the polypeptide of SEQ ID NO:2.

3. The polynucleotide of claim 1 wherein said polynucleotide comprises the nucleotide sequence set forth in SEQ ID NO:1.

4. The isolated polynucleotide of claim 3 which is DNA or RNA.

5. The isolated polynucleotide of claim 3 consisting of the nucleotide sequence set forth in SEQ ID NO:1.

6. The polynucleotide of claim 1 which is DNA or RNA.

7. An isolated expression system comprising a DNA or RNA molecule, wherein said expression system is capable of producing a SDR2 polypeptide comprising the amino acid sequence of SEQ ID NO:2 when said expression system is present in a compatible host cell.

8. A host cell comprising the expression system of claim 7.

9. A process for producing a SDR2 polypeptide comprising culturing a host of claim 8 under conditions sufficient for the production of said polypeptide and recovering the polypeptide from the culture.

10. A process for producing a cell which produces a SDR2 polypeptide comprising the transformation or transfection of a host cell with the expression system of claim 7 such that the host cell, under appropriate culture conditions, produces a SDR2 polypeptide.

11. A recombinant host cell expressing the polypeptide produced by the method of claim 10.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 1803 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

```
TTTTATCAGA TGGCAGTTTC TGGATTTACT CTTGGTACCT GCATACTTCT GTTGCACATT    60

AGTTATGTGG CTAATTATCC CAATGGAAAA GTAACACAGT CATGCCATGG AATGATTCCT   120

GAACATGGTC ATAGTCCACA GTCTGTTCCT GTTCATGACA TTTACGTGAG TCAGATGACA   180

TTCAGGCCAG GAGATCAGAT TGAAGTTACT TTGTCAGGGC ATCCATTTAA AGGCTTTCTC   240

CTAGAAGCGC GTAATGCTGA GGATCTGAAT GGCCCTCCTA TTGGCTCCTT CACATTGATT   300

GACAGTGAAG TGTCACAACT TTTGACCTGT GAAGATATAC AGGGATCAGC AGTGAGTCAC   360

AGAAGTGCAT CTAAAAAAAC AGAAATTAAA GTCTACTGGA ATGCTCCAAG CAGTGCTCCA   420

AATCACACAC AGTTTCTAGT CACAGTTGTT GAGAAGTATA AAATCTACTG GGTGAAGATT   480

CCTGGTCCTA TAATTTCACA ACCAAATGCA TTTCCTTTTA CAACACCTAA AGCTACAGTA   540

GTACCTTTGC CAACGTTACC TCCCGTTTCC CACTTAACCA AACCATTCAG TGCCTCAGAT   600

TGTGGGAACA AGAAGTTCTG TATTAGGAGT CCTTTGAACT GTGACCCAGA GAAGGAGGCT   660

TCCTGTGTCT TCTTGTCCTT CACAAGAGAT GACCAATCGG TGATGGTTGA AATGAGCGGC   720

CCCAGTAAAG GCTATTTATC CTTTGCATTG TCTCATGATC AGTGGATGGG TGATGATGAT   780

GCTTATCTGT GTATTCATGA AGATCAGACT GTGTACATCA AGCCTTCCCA TTTAACGGGG   840

CGAAGTCACC CTGTAATGGA CTCCAGGGAT ACCCTTGAGG ATATGGCTTG GAGGTTGGCG   900

GACGGTGTTA TGCAGTGTTC TTTCAGAAGA AACATTACCC TTCCTGGAGT TAAGAATAGA   960

TTTGATCTAA ACACAAGCTA TTACATATTT CTAGCAGATG GTGCAGCTAA TGATGGTCGA  1020

ATTTACAAGC ACTCTCAGCA ACCTTTGATT ACCTATGAAA AATATGATGT GACAGACTCT  1080

CCAAAGAACA TAGGAGGATC CCATTCTGTA CTCCTTCTGA AGGTTCATGG TGCCTTAATG  1140

TTTGTGGCAT GGATGACTAC TGTTAGCATA GGTGTACTGG TTGCCCGGTT CTTCAAGCCA  1200

GTTTGGTCAA AAGCTTTCTT GCTTGGTGAA GCAGCTTGGT TTCAGGTGCA TCGGATGCTC  1260

ATGTTCACCA CAACTGTCCT CACCTGCATT GCTTTTGTTA TGCCGTTTAT ATACAGGGGA  1320

GGCTGGAGTA GGCATGCAGG TTACCACCCA TACCTCGGCT GTATAGTGAT GACTTTGGCA  1380

GTTCTTCAGC CTCTTCTGGC AGTCTTCAGG CCACCTTTAC ATGACCCAAG AAGGCAAATG  1440

TTTAACTGGA CTCATTGGAG TATGGGAACA GCTGCTAGAA TAATAGCAGT GGCAGCGATG  1500

TTCCTGGGAA TGGATTTACC AGGACTGAAT CTTCCTGATT CATGGAAAAC CTATGCAATG  1560

ACCGGATTCG TAGCCTGGCA TGTTGGGACT GAGGTTGTTC TGGAGGTACA TGCTTATCGG  1620

CTCTCTCGCA AAGTTGAAAT ATTGGATGAT GACAGAATTC AGATCCTTCA GTCATTTACT  1680

GCAGTGGAAA CAGAGGGTCA TGCTTTTAAA AAGGCAGTGT TGGCAATTTA TGTCTGTGGG  1740

AATGTTACTT TTCTCATCAT ATTTTTATCT GCAATCAACC ATCTATGAGC AAGACTCTGT  1800
```

CTC                                                                                                                  1803

(2) INFORMATION FOR SEQ ID NO:2:

(i) SEQUENCE CHARACTERISTICS:
        (A) LENGTH: 592 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Ala Val Ser Gly Phe Thr Leu Gly Thr Cys Ile Leu Leu Leu His
  1               5                  10                  15

Ile Ser Tyr Val Ala Asn Tyr Pro Asn Gly Lys Val Thr Gln Ser Cys
             20                  25                  30

His Gly Met Ile Pro Glu His Gly His Ser Pro Gln Ser Val Pro Val
         35                  40                  45

His Asp Ile Tyr Val Ser Gln Met Thr Phe Arg Pro Gly Asp Gln Ile
     50                  55                  60

Glu Val Thr Leu Ser Gly His Pro Phe Lys Gly Phe Leu Glu Ala
 65                  70                  75                  80

Arg Asn Ala Glu Asp Leu Asn Gly Pro Pro Ile Gly Ser Phe Thr Leu
             85                  90                  95

Ile Asp Ser Glu Val Ser Gln Leu Leu Thr Cys Glu Asp Ile Gln Gly
            100                 105                 110

Ser Ala Val Ser His Arg Ser Ala Ser Lys Lys Thr Glu Ile Lys Val
            115                 120                 125

Tyr Trp Asn Ala Pro Ser Ser Ala Pro Asn His Thr Gln Phe Leu Val
        130                 135                 140

Thr Val Val Glu Lys Tyr Lys Ile Tyr Trp Val Lys Ile Pro Gly Pro
145                 150                 155                 160

Ile Ile Ser Gln Pro Asn Ala Phe Pro Phe Thr Thr Pro Lys Ala Thr
                165                 170                 175

Val Val Pro Leu Pro Thr Leu Pro Pro Val Ser His Leu Thr Lys Pro
            180                 185                 190

Phe Ser Ala Ser Asp Cys Gly Asn Lys Lys Phe Cys Ile Arg Ser Pro
        195                 200                 205

Leu Asn Cys Asp Pro Glu Lys Glu Ala Ser Cys Val Phe Leu Ser Phe
    210                 215                 220

Thr Arg Asp Asp Gln Ser Val Met Val Glu Met Ser Gly Pro Ser Lys
225                 230                 235                 240

Gly Tyr Leu Ser Phe Ala Leu Ser His Asp Gln Trp Met Gly Asp Asp
                245                 250                 255

Asp Ala Tyr Leu Cys Ile His Glu Asp Gln Thr Val Tyr Ile Gln Pro
            260                 265                 270

Ser His Leu Thr Gly Arg Ser His Pro Val Met Asp Ser Arg Asp Thr
        275                 280                 285

Leu Glu Asp Met Ala Trp Arg Leu Ala Asp Gly Val Met Gln Cys Ser
    290                 295                 300

Phe Arg Arg Asn Ile Thr Leu Pro Gly Val Lys Asn Arg Phe Asp Leu
305                 310                 315                 320

Asn Thr Ser Tyr Tyr Ile Phe Leu Ala Asp Gly Ala Ala Asn Asp Gly
                325                 330                 335
```

```
Arg Ile Tyr Lys His Ser Gln Gln Pro Leu Ile Thr Tyr Glu Lys Tyr
            340                 345                 350

Asp Val Thr Asp Ser Pro Lys Asn Ile Gly Gly Ser His Ser Val Leu
            355                 360                 365

Leu Leu Lys Val His Gly Ala Leu Met Phe Val Ala Trp Met Thr Thr
            370                 375                 380

Val Ser Ile Gly Val Leu Val Ala Arg Phe Phe Lys Pro Val Trp Ser
385                 390                 395                 400

Lys Ala Phe Leu Leu Gly Glu Ala Ala Trp Phe Gln Val His Arg Met
                405                 410                 415

Leu Met Phe Thr Thr Thr Val Leu Thr Cys Ile Ala Phe Val Met Pro
                420                 425                 430

Phe Ile Tyr Arg Gly Gly Trp Ser Arg His Ala Gly Tyr His Pro Tyr
            435                 440                 445

Leu Gly Cys Ile Val Met Thr Leu Ala Val Leu Gln Pro Leu Leu Ala
            450                 455                 460

Val Phe Arg Pro Pro Leu His Asp Pro Arg Arg Gln Met Phe Asn Trp
465                 470                 475                 480

Thr His Trp Ser Met Gly Thr Ala Ala Arg Ile Ile Ala Val Ala Ala
                485                 490                 495

Met Phe Leu Gly Met Asp Leu Pro Gly Leu Asn Leu Pro Asp Ser Trp
                500                 505                 510

Lys Thr Tyr Ala Met Thr Gly Phe Val Ala Trp His Val Gly Thr Glu
            515                 520                 525

Val Val Leu Glu Val His Ala Tyr Arg Leu Ser Arg Lys Val Glu Ile
530                 535                 540

Leu Asp Asp Asp Arg Ile Gln Ile Leu Gln Ser Phe Thr Ala Val Glu
545                 550                 555                 560

Thr Glu Gly His Ala Phe Lys Lys Ala Val Leu Ala Ile Tyr Val Cys
                565                 570                 575

Gly Asn Val Thr Phe Leu Ile Ile Phe Leu Ser Ala Ile Asn His Leu
            580                 585                 590

(2) INFORMATION FOR SEQ ID NO:3:

(i) SEQUENCE CHARACTERISTICS:
        (A) LENGTH: 391 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GGTTCATGAC ATTTACGTGA GTCAGATGAC ATTCAGGCCA GGAGATCAGA TTGAAGTTAC    60

TTTGTCAGGG CATCCATTTA AAGGCTTTCT CCTAGAAGCG CGTAATGCTG AGGATCTGAA   120

TGGCCCTCCT ATTGGCTCCT TCACATTGAT TGACAGTGAA GTGTCACAAC TTTTGACCTG   180

TGAAGATATA CAGGGGATCA GCAGTGAGTC ACAGAAGTGG CATCTGAAAA AAACAGAAAT   240

TAAAGTCTAC TGGGAAGCTC CAAGCAGTGG CTCCCAAATG CACACACAGT TCTAGTGAC    300

AGTTGTTGAG AAGATGAAAA TCTACTGGGT GAAGATTNCC TGGTGCCCAT GATTTTGCAC   360

AACCAAANGG CATTTGCCTT TTTTACNAAC A                                  391

(2) INFORMATION FOR SEQ ID NO:4:

(i) SEQUENCE CHARACTERISTICS:
```

```
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Val His Asp Ile Tyr Val Ser Gln Met Thr Phe Arg Pro Gly Asp Gln
1               5                   10                  15

Ile Glu Val Thr Leu Ser Gly His Pro Phe Lys Gly Phe Leu Leu Glu
                20                  25                  30

Ala Arg Asn Ala Glu Asp Leu Asn Gly Pro Pro Ile Gly Ser Phe Thr
            35                  40                  45

Leu Ile Asp Ser Glu Val Ser Gln Leu Leu Thr Cys Glu Asp Ile Gln
        50                  55                  60

Gly Ile Ser Ser Glu Ser Gln Lys Trp His Leu Lys Lys Thr Glu Ile
65                  70                  75                  80

Lys Val Tyr Trp Glu Ala Pro Ser Ser Gly Ser Gln Met His Thr Gln
                85                  90                  95

Phe Leu Val Thr Val Val Glu Lys Met Lys Ile Tyr Trp Val Lys Ile
                100                 105                 110
```